US00PP26891P2

(12) United States Plant Patent
Williams

(10) Patent No.: US PP26,891 P2
(45) Date of Patent: Jun. 28, 2016

(54) ***COLOCASIA* PLANT NAMED 'VICTORIOUS GIGANTE'**

(50) Latin Name: ***Colocasia* hybrid**
Varietal Denomination: Victorious Gigante

(71) Applicant: Brian Paul Williams, Louisville, KY (US)

(72) Inventor: Brian Paul Williams, Louisville, KY (US)

(73) Assignee: Brian's Botanicals, Louisville, KY (US)

( * ) Notice: Subject to any disclaimer, the term of this patent is extended or adjusted under 35 U.S.C. 154(b) by 175 days.

(21) Appl. No.: 13/999,226

(22) Filed: Jan. 31, 2014

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Keith Robinson
(74) *Attorney, Agent, or Firm* — Penny J. Aguirre

(57) ABSTRACT

A new cultivar of *Colocasia* plant named 'Victorious Gigante' that is characterized by its very large leaves that are light green in color on the upper surface and grey-green on the lower surface and held horizontal on petiole, its leaves with a rugose surface and cupped edges to form a bowl shape, and its small tuberous rhizomes at the base of the plant that become large tubers with age.

2 Drawing Sheets

Botanical classification: *Colocasia* hybrid.
Cultivar designation: 'Victorious Gigante'.

BACKGROUND OF THE INVENTION

The present invention, *Colacasia* 'Victorious Gigante', relates to a new and distinct interspecific hybrid of *Colacasia*, hereinafter referred to by its cultivar name, 'Victorious Gigante'. 'Victorious Gigante' is a new tropical plant used as a landscape and container plant in tropical and subtropical areas.

The new cultivar was derived from a controlled breeding program conducted by the Inventor at his nursery in Louisville, Ky. The overall purpose of the breeding program is to make selections of *Colocasia* plants that are unique with large leaves and vigorous growth habits. 'Victorious Gigante' arose from a cross made in June of 2010 between an unnamed plant of a *Colocasia* of hybrid origin from the Inventor's breeding program as the female parent and an unnamed plant of *Colocasia gigantea* as the male parent. 'Victorious Gigante' was selected as a single unique plant in June of 2013 from amongst the seedlings derived from the above cross.

Asexual propagation of the new cultivar was first accomplished by in vitro propagation under the direction of the Inventor in Eustis, Fla. in November of 2013. Asexual propagation by in vitro propagation has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'Victorious Gigante' as a new and unique cultivar of *Colocasia.*

1. 'Victorious Gigante' exhibits very large leaves, up to 1 m in length.

2. 'Victorious Gigante' exhibits leaves that are light green in color on the upper surface and grey-green on the lower surface and held horizontal to petiole.
3. 'Victorious Gigante' exhibits leaves with a rugose surface and cupped edges to form a bowl shape.
4. 'Victorious Gigante' exhibits petioles that are dark pink in color and mature to an orange-pink color.
5. 'Victorious Gigante' exhibits small tuberous rhizomes at the base of the plant with large tubers produced with age.

The female parent of 'Victorious Gigante', an unnamed plant of *Colocasia* of hybrid origin, differs from 'Victorious Gigante' in having smaller leaves that are held vertically, in having petioles that are light pink in color, and in lacking cupped leaf margins. The male parent of 'Victorious Gigante', an unnamed plant of *Colocasia gigantea*, differs from 'Victorious Gigante' in in lacking cupped leaf margins, in having petioles that are green in color, and in lacking tuberous rhizomes. 'Victorious Gigante' can be most closely compared to the *Colocasia esculenta* cultivars 'Black Magic' (not patented) and 'Mojito' (U.S. Plant Pat. No. 21,995). Both are similar to 'Victorious Gigante' in having large leaves. 'Black Magic' differs from 'Victorious Gigante' in being slightly shorter in height, in having leaves and petioles that are black in color, and in rarely producing tubers. 'Mojito' differs from 'Victorious Gigante' in being shorter in height, in having leaves that are variegated (green with black mottling), in having veins that are black in color, and in rarely producing tubers.

BRIEF DESCRIPTION OF THE DRAWINGS

The accompanying colored photographs illustrate the overall appearance and distinct characteristics of the new *Colocasia*, 'Victorious Gigante'. The photographs were taken of a two year-old plants as grown outdoors under 2 mm poly greenhouse plastic and natural lighting in Louisville, Ky. and planted in a raised bed.

Figure 1:
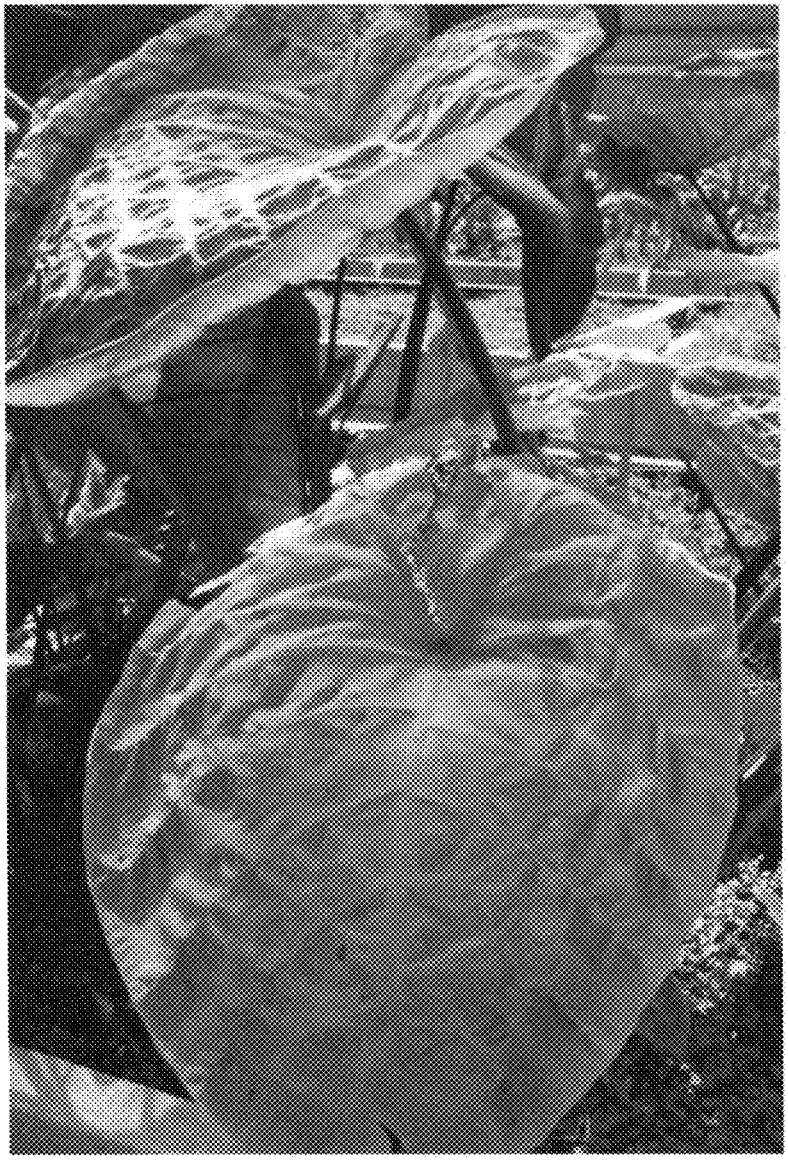
FIG. 1 provides a view of the foliage with cupped margins and the petiole color of 'Victorious Gigante'.
Figure 2:
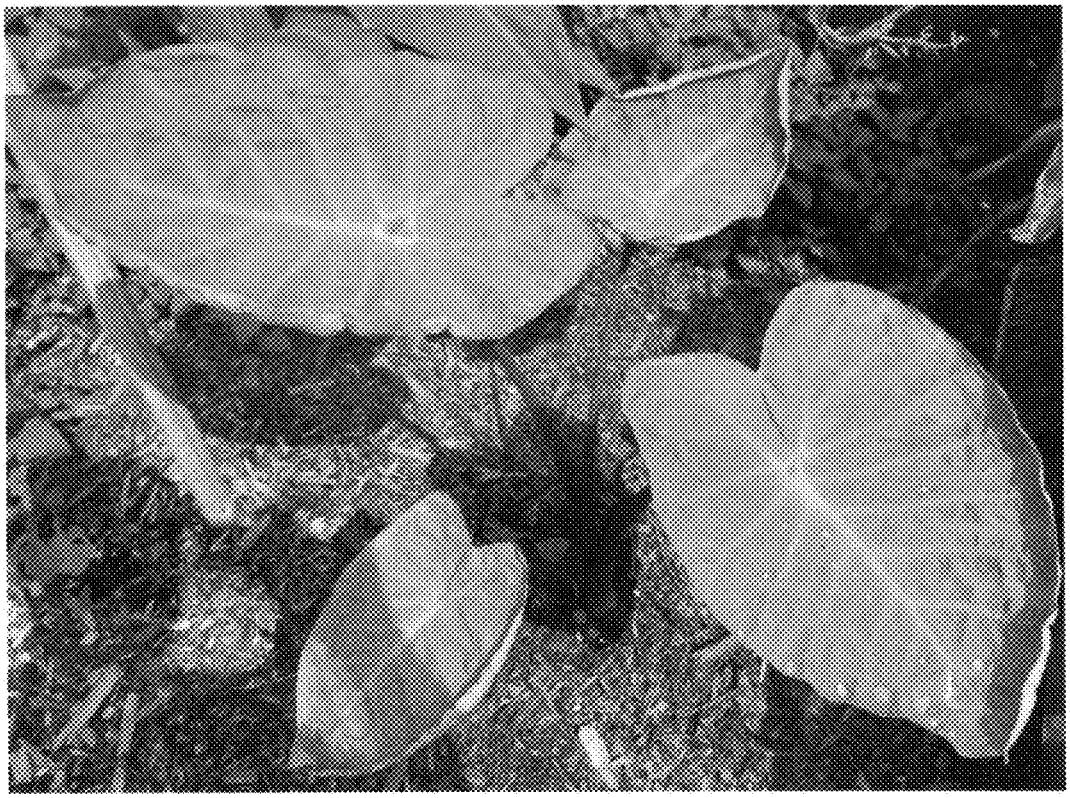

The photograph in FIG. 2 provides a view of the petiole color as the leaves mature of 'Victorious Gigante'.

The colors in the photographs are as close as possible with the photographic and printing technology utilized and the color values cited in the Detailed Botanical Description accurately describe the colors of the new *Colocasia*.

DETAILED BOTANICAL DESCRIPTION OF THE PLANT

The following is a detailed description of two year-old plants of the new cultivar as grown outdoors in full sun under 2 mm poly greenhouse plastic in Louisville, Ky. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Tropical perennial.

*Plant habit.*—Upright, stemless.

*Height and spread.*—Reaches 1.2 to 1.8 m (4 to 6 ft) in height and 0.9 to 1.5 m (3 to 5 ft) in width.

*Cold hardiness.*—At least to U.S.D.A. Zone 7.

*Diseases.*—No particular resistance or susceptibility has been observed.

*Roots.*—Fleshy.

*Propagation type.*—In vitro propagation is preferred.

*Growth rate.*—Vigorous.

*Stem description.*—Stemless.

*Tuberous rhizomes.*—Form at base of plant, scales 165A in color, tubers observed up to 10 cm in diameter with age.

Foliage description:

*Leaf shape.*—Ovate-slightly oblong.

*Leaf division.*—Single.

*Leaf base.*—Cordate.

*Leaf apex.*—Acute, slightly cuspidate.

*Leaf venation.*—Pinnate, young upper surface; 144A, young lower surface; 146A, mature upper and lower surface; 138D with the area of petiole attachment suffused with 183A on upper surface.

*Leaf margins.*—Slightly undulate and cupped to form a bowl shape.

*Leaf attachment.*—Petiolate.

*Leaf arrangement.*—Alternate.

*Leaf surface.*—Upper surface; glabrous, rugose, and satiny, lower surface; dull and rugose.

*Leaf orientation.*—Held horizontal on petiole.

*Leaf color.*—Young upper surface; blend of 139A and 138A, blending into 144B towards margins, with a flush of 144B between veins, young lower surface; blend of 137A and 137B, blending into 144A towards margins with a flush of 144B between veins, mature upper surface; a blend of 138A and 144A, mature lower surface; 191D.

*Leaf size.*—Up to 1 m in length and 50 cm in width.

*Petioles.*—Held erect to semi-erect, an average of 1.2 m in length and 4 cm in distal diameter and 1 cm in proximal diameter, glabrous and slightly glaucous surface, young leaves 183A in color, mature leaves closest to 163C in color and slightly suffused with 183A.

Inflorescence description:

*Inflorescence type.*—Spadix surrounded by a spathe.

*Inflorescence size.*—Average of 44 cm in length and 2.3 cm in diameter.

*Inflorescence bud.*—Linear to slightly narrow oblanceolate in shape, an average of 12.5 in length and 2.2 cm in width, 145C in color.

*Flower fragrance.*—None.

*Lastingness of inflorescence.*—Inflorescence blooms intermittently during the bloom period, individual flowers last about 2 to 3 weeks.

*Inflorescence/flower quantity.*—Intermittent throughout the bloom season, an average of 200 female flowers per spadix and 1 male flower.

*Spathe.*—Hooded, bract, subtending spadix, ovate in shape, entire margin, acute apex, coriaceous surface, 10.5 cm in length and 5.5 cm in width, lasts 5 to 7 days, color: when opening and fully open on inner surface; 158B and outer rear surface; a blend of 154D, 162C and 184C, fading to a blend of 176A and 199C.

*Spadix.*—Male portion above female zone, upright cylindrical shape (phallus-like), apex narrowly pointed, about 1.4 cm in diameter (not including ovary) and 11 cm in length, male zone; 9.5 mm in diameter and 8.5 cm in length, color; immature and mature a mix of 72B and 159A, female zone; 1.4 cm in diameter and 2.5 cm length, color immature and mature a blend of 150C to 150D and 160C.

*Peduncle.*—Emerges from base of plant, up to 30 cm in length and 14 mm in diameter, held upright, color; a blend between 182A and 184B to 184D maturing to; a blend of 148A, 184C, N186B and 199A, glaucous surface.

Reproductive organs:

*Gynoecium.*—Stigmas are 182A in color, ovary is flattened globular in shape and a blend of 11C and 145B in color.

*Androcoecium.*—Undeveloped.

*Fruit and seed.*—Sterile.

It is claimed:

1. A new and distinct cultivar of *Colocasia* plant named 'Victorious Gigante' as herein illustrated and described.

* * * * *